United States Patent [19]

Bolon et al.

[11] Patent Number: 4,533,504

[45] Date of Patent: * Aug. 6, 1985

[54] PROCESS FOR THE PREPARATION OF DIARYL CARBONATES

[75] Inventors: Donald A. Bolon, Scotia; Thomas B. Gorczyca, Schenectady; John E. Hallgren, Scotia, all of N.Y.

[73] Assignee: General Electric Company, Schenectady, N.Y.

[*] Notice: The portion of the term of this patent subsequent to Jun. 5, 2001 has been disclaimed.

[21] Appl. No.: 338,189

[22] Filed: Jan. 8, 1982

[51] Int. Cl.$^3$ .................. C07C 68/04; C07C 68/06
[52] U.S. Cl. .................................................. 260/463
[58] Field of Search ............... 568/301, 302; 560/130; 260/463

[56] References Cited

U.S. PATENT DOCUMENTS

| | | | |
|---|---|---|---|
| 2,175,811 | 10/1939 | Loder | 568/301 |
| 3,114,762 | 12/1963 | Mador et al. | 260/463 |
| 3,227,740 | 1/1966 | Fenton | 260/463 |
| 3,622,612 | 11/1971 | Muller | 260/463 |
| 3,679,739 | 7/1972 | Schulz et al. | 560/130 |
| 3,846,468 | 11/1974 | Perrotti et al. | 260/463 |
| 3,952,045 | 4/1976 | Gaenzler et al. | 260/463 |
| 4,045,464 | 8/1977 | Romano et al. | 260/463 |
| 4,131,521 | 12/1978 | Cipris et al. | 204/59 |
| 4,182,726 | 1/1980 | Illuminati et al. | 260/463 |
| 4,252,737 | 2/1981 | Krimm et al. | 260/463 |

*Primary Examiner*—Donald G. Daus
*Assistant Examiner*—Diana G. Rivers
*Attorney, Agent, or Firm*—William H. Pittman; James C. Davis, Jr.; James Magee, Jr.

[57] ABSTRACT

Diaryl and substituted diaryl carbonates are formed by a series of steps, the first step involving the production of a dialkyl carbonate from an alkanol, carbon monoxide and oxygen; and the second step involving the reaction of the dialkyl carbonate with a phenyl ester or substituted phenyl ester in the presence of a dialkyl tin compound to produce a mixture of diaryl carbonate, alkyl aryl carbonate, and an alkyl ester. The alkyl ester can be heated to reform the alkanol and form ketene; in turn the ketene can be reacted with the phenol or substituted phenol to form the phenyl ester or substituted phenyl ester used in the second step above.

7 Claims, No Drawings

PROCESS FOR THE PREPARATION OF DIARYL CARBONATES

BACKGROUND OF THE INVENTION

A number of routes for the production of polycarbonate resins are presently available, and some of these are employed commercially. Generally, the commercial processes involve the use of phosgene, but the avoidance of use of such phosgene is desired, because of the toxicity of the material and environmental problems it may generate.

A particularly desirable route to such polycarbonate resins would involve the use of a diaryl or substituted diaryl carbonate. However, while a number of processes have been described for the production of such diaryl carbonates, none to our knowledge not involving phosgene have proved economically feasible.

CROSS-REFERENCE TO RELATED APPLICATIONS

A major reactant employed in accordance with the present invention is a dialkyl carbonate. One particularly desirable method for producing such a dialkyl carbonate is described and claimed in copending application filed Nov. 9, 1981 now U.S. Pat. No. 4,360,477—Hallgren and Lucas, for "Carbonylation of Alkanols", assigned to the same assignee as the present invention, and incorporated herein by reference.

Additionally, a process similar to the process of the present invention, in that it involves an integrated process, for the production of polycarbonate resins is described and claimed in copending application, Ser. No. 479,049, filed Mar. 25, 1983, now U.S. Pat. No. 4,452,968, by Bolon and Hallgren, assigned to the same assignee as the present invention, and entitled "Synthesis of Polycarbonates".

SUMMARY OF THE INVENTION

In accordance with the present invention, a process is described for the preparation of diaryl and substituted diaryl carbonates from phenol or substituted phenols, carbon monoxide, and oxygen. The primary intermediates employed in the process, which involves a number of steps, are dialkyl carbonates and a phenyl or substituted phenyl ester, the latter components being employed in an ester interchange reaction.

In the preferred mode of carrying out the present invention, the following steps are involved:

1. synthesis of the dialkyl carbonate, particularly dimethyl carbonate, from an alkanol, oxygen, and carbon monoxide;

2. an ester interchange reaction between the dialkyl carbonate produced according to step 1 and a phenyl or substituted phenyl ester, particularly phenyl acetate, in the presence of a dialkyl tin catalyst, to form the diaryl or substituted diaryl carbonate and an alkyl aryl carbonate, along with an alkyl ester;

3. thermolysis of the alkyl ester produced according to step 2, particularly methyl acetate, to produce a ketene and reform the alkanol. The phenyl or substituted phenyl ester, particularly the phenyl acetate, is produced from phenol and the ketene resulting in step 3. The alkanol, particularly methanol, produced in step 3, is recycled to step 1. The mixture of diaryl carbonate and alkyl aryl carbonate produced in step 2 can be further heated to complete the reaction to the diaryl carbonate.

Thus, in accordance with the present invention, diaryl carbonates and substituted diaryl carbonates are produced according to equation 1:

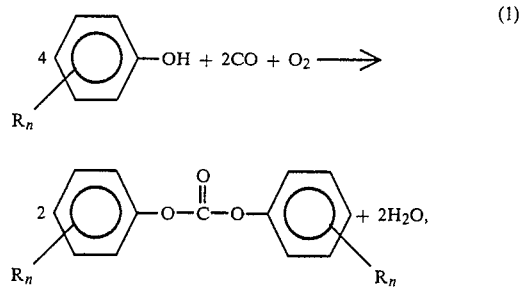

(1)

where R is independently selected from the class consisting of alkyl (e.g., methyl, ethyl, propyl, isopropyl, butyl, etc.) alkoxy (e.g. methoxy, ethoxy, isopropoxy, etc.), aryl (e.g. phenyl, tolyl, xylyl, etc.), and aryloxy groups (e.g., phenoxy, tolyloxy, etc.); and n is a whole number from 0 to 3.

DESCRIPTION OF THE PREFERRED EMBODIMENTS

In accordance with the present invention, an integrated process for the production of diaryl and substituted diaryl carbonates from phenol and substituted phenols, carbon monoxide, and oxygen has been discovered in accordance with the above described equation 1.

Generally, the reactions included in the integrated process are the following:

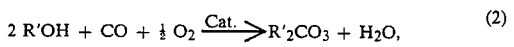

(2)

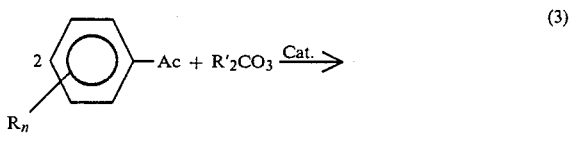

(3)

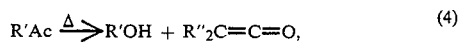

(4)

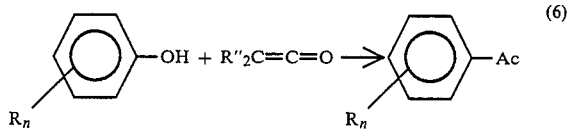

(6)

where R and n are as previously defined, R' is an alkyl group from a primary, secondary, or tertiary alcohol, Ac is an acyloxy radical of the formula

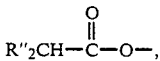

wherein each R″ is hydrogen or alkyl, and R″₂C═C═O is the ketene formed by thermolysis of R′Ac. Preferably, R′ is selected from the group consisting of methyl, ethyl, isopropyl, and butyl; and Ac is selected from the class consisting of acetoxy, propionoxy, and butyroxy which restricts each R″ to being independently selected from the group consisting of hydrogen, methyl and ethyl for the preferred embodiment. Most preferably, from the standpoint of ease of reaction and utilization of the finally prepared materials, n is 0, R′ is methyl, Ac is acetoxy, and each R″ is H.

The production of dialkyl carbonates, particularly dimethyl carbonate, from an alkanol, carbon monoxide, and oxygen is described in a number of places. For example, a preferred method of forming the dialkyl carbonate, particularly dimethyl carbonate, is shown in the aforesaid copending application now U.S. Pat. No. 4,360,477. Other methods for forming the dialkyl carbonates are shown, for example, in the following U.S. Pat. Nos.:

3,114,762—Mador et al
3,227,740—Fenton
3,846,468—Perrotti et al
3,952,045—Gaenzler
4,131,521—Cipris et al Since it is desired that the polycarbonates produced in accordance with the present invention, as the final desired product, be as colorless as possible, the dialkyl carbonate is preferably purified prior to utilization in equation (3) of the overall reaction of the present invention. For example, dimethyl carbonate may contain, as impurities, hydrocarbons, water, methanol, amines, and electrolytes, as well as other organics. One purification scheme that has been found to be acceptable is the extraction of dimethyl carbonate with an equal volume of water, followed by a careful distillation to remove the water-dimethyl carbonate azeotropic mixture.

In the second step of the process for production of a diaryl or substituted diaryl carbonate, there is an ester interchange reaction between a phenyl or substituted phenyl ester and the dialkyl carbonate produced in accordance with equation (2). The reaction between the phenyl or substituted phenyl ester and the dialkyl carbonate is a catalytic reaction and, generally, is carried out in two stages. The first stage is usually carried out at a temperature of from 150° to 300° C., preferably, at 180° to 250° C. There appears to be no economic advantage in proceeding at temperatures over 250° C. Generally, the reaction requires about one-half hour at 180° C. and from five to ten minutes at 220° C. The reactants are employed in a stoichiometric ratio.

Pressure is required in this reaction in order to allow heating of the reaction mixture to temperatures over 150° C. Generally, the pressure range employed is from 100 to 350, or more, psig. Preferably, the pressure is above 200 psig. This allows the alkyl acylate, particularly methyl acetate to be distilled over. The material remaining in the reaction vessel after distillation of the alkyl acylate is, generally, a mixture of the diaryl or substituted diaryl carbonate, an aryl or substituted aryl alkyl carbonate and the remaining dialkyl carbonate. This is converted to the maximum yield of diaryl or substituted diaryl carbonate in a second step of the reaction. This second step of the reaction is carried out at from 200° to 240° C. at from atmospheric pressure to 40 psig. At lower temperatures, atmospheric pressure is employed, while at higher temperatures, the use of pressure is required. Preferably, this second step of the reaction is carried out at from 200° to 220° C. at atmospheric pressure.

Both steps of the ester interchange reaction, the second step being, essentially, a carbonate interchange, are carried out in the presence of a catalyst. The catalyst employed is:

$$X_2SnY_2 \qquad (5)$$

where X is a $C_{1-8}$ alkyl substituent and either each Y is independently selected from the class consisting of OX, acyloxy, or halogen or both Y's are taken together to define oxygen. The amount of the tin catalyst of formula (5) employed is from 50 to 1000 ppm, preferably from 500 to 1000 ppm, based on the weight of the initial reactants in the ester interchange reaction.

Employing these catalysts, the residue in the pot, after removal of the diaryl or substituted diaryl carbonate, by distillation, can be recycled for the next ester interchange reaction, without diminution of activity. The preferred catalyst, of formula (5), because of cost is $(C_4H_9)_2SnO$.

In the last step of the integrated process, the alkyl ester, preferably methyl acetate, is heated, in order to regenerate the alkanol employed in step 1 and a ketene. The particular ketene produced will, of course, depend upon the particular alkyl ester which is heated. When the preferred methyl acetate is heated, ketene is the result. The ketene is reacted with the appropriate phenol to produce a phenyl ester for use in the step of the reaction described in accordance with equation (3). Thus, in the preferred embodiment, ketene is reacted with phenol to produce phenyl acetate, which is described in the prior art.

Thus, an integrated process has been described for the formation of a diaryl or substituted diaryl carbonate employing, as raw materials, phenol or substituted phenol, carbon monoxide, and oxygen. As described above, the carbon monoxide and oxygen are reacted with an alkanol to produce a dialkyl carbonate, the dialkyl carbonate is reacted with a phenyl ester or substituted phenyl ester to produce a diaryl or substituted diaryl carbonate and an alkyl ester; the resulting alkyl ester is heated to produce the alkanol employed in the first step and a ketene, the ketene being reacted with phenol or substituted phenol to regenerate the phenyl or substituted phenyl ester employed in the second step of the process.

While an ester interchange between phenyl and substituted phenyl esters and dialkyl carbonates to produce diaryl carbonate or aryl alkyl carbonate has been shown, as, for example in Illuminati et al U.S. Pat. No. 4,182,726, a different catalyst was employed. As indicated, above, in the description of the catalyst employed in this reaction according to the present invention, shown in formula (5), the tin catalyst has two alkyl substituents. The catalyst employed by Illuminati et al excludes such an alkyl containing catalyst, showing halogen, acetoxy, alkoxy, and aryloxy. Recycling of the catalyst is neither shown nor described in Illuminati et al. Catalysts similar to those of Illuminati et al for forming diaryl carbonates from phenyl alkyl carbonates, without a description of recyclability of the catalyst, are shown in Romano et al U.S. Pat. No. 4,045,464.

Attempts to carry out the same general reactions as set forth herein, wherein phenol was reacted with dimethyl carbonate were attempted. The same catalyst as employed here, including particularly, dibutyl tin dibutoxide, and dibutyl tin oxide, were tried. Yields were low, and reaction times were excessive.

The formation of dialkyl carbonates from alkanol, carbon monoxide, and oxygen will not be detailed in this application. That portion of the aforementioned U.S. Pat. No. 4,360,477 providing specific examples for the preparation of such materials is herein incorporated by reference.

The remaining steps of the reaction, in accordance with the present invention, will be illustrated below. The examples set forth should not be considered as limiting, in any way, the full scope of the invention. All parts in the examples, unless otherwise indicated, are by weight.

EXAMPLE 1

A stainless steel pressure vessel containing a stainless steel distillation column packed with protruded monel packing material and a condenser was employed. The receiver was charged with 109 grams dimethyl carbonate, 272 grams phenyl acetate, and 0.068 grams dibutyl tin dibutoxide. The reaction mixture was pressurized at 200 psig and was heated under this pressure to 220° C. where distillation of methyl acetate commenced at a head temperature of 150°–160° C. After 30 to 60 minutes, the temperature at the head dropped and the pot mixture was cooled to room temperature and analyzed by both gas chromatography and high pressure liquid chromatography. The product analysis was as follows:

TABLE 1

| Compound | Weight (grams) |
| --- | --- |
| A. Distillate | |
| Methyl acetate | 78 |
| Dimethyl carbonate | 2 |
| B. Pot Residue | |
| Phenyl acetate | 62.3 |
| Diphenyl carbonate | 66.5 |
| Phenyl methyl carbonate | 117.1 |
| Dimethyl carbonate | 10.3 |
| Methyl acetate | 37.0 |
| *Tin | *500 ppm |

*Calculated As $SnO_2$

Other catalysts within formula (5), including $(C_4H_9)_2SnO$, $(CH_3)_2Sn(OCH_3)_2$, $(C_4H_9)_2SnCl_2$ and $(C_4H_9)Sn(OCH_3)_2$, were employed in the same manner as set forth in Example 1, and the ultimate product distribution, both distillate and residue, were found to be essentially in the same distribution ratios.

EXAMPLE 2

The pot residue of Example 1, was placed in a glass reaction vessel equipped for distillation. The mixture was heated to 220° C. for about one hour, while distilling methyl acetate and dimethyl carbonate from the reaction mixture. The product analysis is as follows:

TABLE 2

| Component | Wt. (grams) |
| --- | --- |
| Pot Residue from Example 1 | |
| Phenyl acetate | 62.3 |
| Phenyl methyl carbonate | 117.1 |
| Diphenyl carbonate | 66.5 |
| Methyl acetate | 10.3 |
| Dimethyl carbonate | 37.0 |
| $Sn^4$ | (500 ppm of total mixture calculated as $SnO_2$) |
| Overhead | |

TABLE 2-continued

| Component | Wt. (grams) |
| --- | --- |
| Methyl acetate | 71.0 |
| Dimethyl carbonate | 28.2 |
| Pot Residue | |
| Diphenyl carbonate | 203.3 |
| Phenyl methyl carbonate | 6.1 |
| Phenyl acetate | 0.5 |

Pure diphenyl carbonate was isolated from the pot residue by simple vacuum distillation. The catalyst shown in the charge for this example was the catalyst remaining in the residue of Example 1. There was no addition or purification of the materials. The catalyst remaining after the vacuum distillation of the diphenyl carbonate was recycled for further use in accordance with reactions of Example 1, with no decrease in catalytic activity.

EXAMPLE 3

Methyl acetate, as produced in Example 2, diluted with nitrogen, was passed through a quartz tube filled with 12.1% $AlpO_4$ on alumina maintained at 700±10° C. Ketene and methanol were the effluents from the reaction tube, the methanol being separated from the ketene by cooling the effluent to −20° C. The production of ketene was not measured directly, but the ketene was trapped by bubbling it through molten phenol containing a trace of mineral acid as a catalyst to produce phenyl acetate.

EXAMPLE 4

In a stainless steel pressure vessel equipped with a distillation column packed with PRO-PAK protruded 0.16 inch stainless steel packing, air condensor, and receiver, and equipped to maintain pressure from a nitrogen regulator, a quantity of 78 parts dimethyl carbonate, 136 parts phenyl acetate, and 0.5 part dibutyl tin dibutoxide was heated, at 200 psig, to 240° C. for one hour, and then at atmospheric pressure for one hour. A quantity of 89 parts (83% of the theorectical) of diphenyl carbonate was isolated. The pot residue, after removal of the diphenyl carbonate by vacuum distillation, amounting to 3.3 parts, was used as a catalyst in the reaction of 132 parts phenyl acetate and 72 parts dimethyl carbonate. A quantity of 78.1 parts of diphenyl carbonate was recovered, along with 4.4 parts of pot residue for recycle. Analysis indicated less than 1 ppm of tin in the resulting diphenyl carbonate.

EXAMPLE 5

A quartz column was packed with 19 parts of pellets prepared by adding 90 parts distilled water and 10 parts of 85% phosphoric acid to 36 parts gamma-alumina pellets. The mixture was swirled periodically for 90 minutes and the liquid decanted. The pellets were washed three times with 100 parts of distilled water, and dried in a stream of nitrogen at 100° C. for 4 hours, and then overnight (about 18 hours), in vacuo, at 200° C. Analysis indicated the presence of 9.4% of calculated $PO_4$, and these were the pellets with which the quartz column was packed. A quantity of 10 parts methyl acetate was vaporized in a stream of nitrogen at one liter per minute and passed through the column over a period of five minutes. The effluent was passed through a cold trap maintained at −20° C., and then through a solution of 47 parts of phenol, 27 parts of methylene chloride, and 0.2 part of trifluoroacetic acid. The trap indicated the presence of 4.7 parts phenyl acetate, and large quantities, estimated at a 65% recovery, of methyl acetate.

Results similar to those obtained in Examples 1 and 2 can be obtained using, as catalyst in place of dibutyl tin dibutoxide, dimethyl tin dioctoxide, dibutyl tin oxide, dicyclohexyl tin dimethoxide, and other catalysts falling within the generic description of formula (5). Further, results similar to those obtained in Examples 1 and 2 can be obtained when a substituted phenol, as shown in equations (1) and (2) is employed in place of phenol, or when other dialkyl carbonates are employed in place of dimethyl carbonate.

While specific examples of the invention have been shown and described, the invention should be considered only as limited by the appended claims.

What we claim and desire to secure by Letters Patent of the United States is:

1. A process for producing diaryl and substituted diaryl carbonates utilizing phenol and substituted phenols, carbon monoxide and oxygen as raw materials, said process comprising the steps of:
   A. reacting an alkanol, carbon monoxide and oxygen to produce a dialkyl carbonate of the formula $R'_2CO_3$ and water, and removing said water;
   B. reacting said dialkyl carbonate of step A with a phenyl ester of the formula

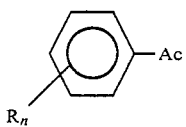

in the presence of a catalyst having the formula $X_2SnY_2$ to produce a diaryl carbonate of the formula

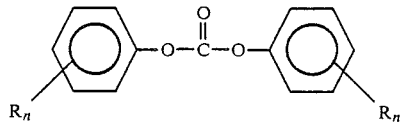

and an alkyl ester of the formula

R'—Ac, said reaction being carried out at a temperature of 150°–250° C. and a pressure of 100–300 psig;
   C. heating said alkyl ester from step B to form a ketene of the formula $R''_2C=C=O$ and the alkanol of step A;
   D. forming the phenyl ester of step B by reacting the corresponding phenol of the formula

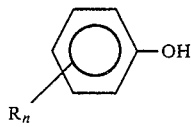

with the ketene of step C; and
   E. recycling the phenyl ester formed in step D to step B and the alkanol formed in step C to step A;
   wherein R is independently selected from the class consisting of alkyl, alkoxy, aryl, and aryloxy groups, R' is an alkyl group from the alkanol, each R'' is hydrogen or alkyl, Ac is an acyloxy radical of the formula

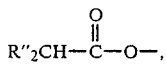

X is a $C_{1-8}$ alkyl substituent, either each Y is independently selected from the class consisting of OX, acyloxy and halogen or both Y's are taken together to define oxygen, and n is a whole number from 0 to 3.

2. The process of claim 1 where n is 0.

3. The process of claim 1 wherein said alkanol is methanol.

4. The process of claim 1 wherein said catalyst is dibutyl tin dibutoxide.

5. The process of claim 1 wherein, subsequent to reaction at 150° to 250° C. at a pressure of 100 to 350 psig, and removal of alkyl ester, reaction is continued at 200° to 250° C. at from atmospheric pressure to 40 psig.

6. The process of claim 5 wherein reaction is carried out at 200° to 220° C. at atmospheric pressure.

7. The process of claim 1 wherein the catalyst of formula $X_2SnY_2$ is recycled for further reaction after recovery of diaryl carbonate.

* * * * *